(12) United States Patent
Youssefi et al.

(10) Patent No.: US 8,740,381 B2
(45) Date of Patent: Jun. 3, 2014

(54) METHOD AND APPARATUS FOR EXTRAPOLATING DIAGNOSTIC DATA

(75) Inventors: Gerhard Youssefi, Landshut (DE); Anton Hilger, München (DE); Julia Hoff, München (DE)

(73) Assignee: Bausch & Lomb Incorporated, Rochester, NY (US)

( * ) Notice: Subject to any disclaimer, the term of this patent is extended or adjusted under 35 U.S.C. 154(b) by 2028 days.

(21) Appl. No.: 11/823,401

(22) Filed: Jun. 27, 2007

(65) Prior Publication Data
US 2009/0006508 A1   Jan. 1, 2009

(51) Int. Cl.
*A61B 3/10* (2006.01)
*A61B 18/18* (2006.01)

(52) U.S. Cl.
CPC ................................ *A61B 3/1015* (2013.01)
USPC ............... 351/205; 351/212; 606/4

(58) Field of Classification Search
USPC ....... 708/290; 600/402, 558; 606/4; 351/205, 351/212
See application file for complete search history.

(56) References Cited

U.S. PATENT DOCUMENTS

| | | | |
|---|---|---|---|
| 6,299,311 B1* | 10/2001 | Williams et al. | 351/221 |
| 6,817,714 B2* | 11/2004 | Altmann | 351/159.74 |
| 7,717,562 B2 | 5/2010 | Dai | 351/212 |
| 2002/0007176 A1* | 1/2002 | Campin et al. | 606/5 |
| 2004/0054358 A1* | 3/2004 | Cox et al. | 606/5 |
| 2004/0057010 A1* | 3/2004 | Altmann | 351/177 |
| 2004/0169820 A1* | 9/2004 | Dai et al. | 351/246 |
| 2005/0213040 A1* | 9/2005 | Gross et al. | 351/243 |
| 2006/0170865 A1* | 8/2006 | Hirohara et al. | 351/205 |
| 2006/0203198 A1* | 9/2006 | Liang | 351/246 |
| 2007/0008491 A1* | 1/2007 | Polland et al. | 351/212 |
| 2007/0058132 A1* | 3/2007 | Dai | 351/246 |
| 2007/0258042 A1* | 11/2007 | Wooley et al. | 351/161 |
| 2007/0258044 A1* | 11/2007 | Norrby et al. | 351/212 |
| 2008/0077644 A1 | 3/2008 | Dai | 708/401 |
| 2009/0141235 A1* | 6/2009 | Collins et al. | 351/160 R |

OTHER PUBLICATIONS

Campbell, *Matrix Method to Find a New Set of Zernike Coefficients From an Original Set When the Aperture Radius is Changed*, J. Opt. Soc. Am. A, Feb. 2003, vol. 20, No. 2, pp. 209-217.

Liang et al., *Objective measurement of wave aberrations of the human eye with the use of a Hartmann-Shack wave-front sensor*, J. Opt. Soc. Am. A, Jul. 1994, vol. 11, No. 7, pp. 1949-1957.

\* cited by examiner

*Primary Examiner* — Miranda Le
(74) *Attorney, Agent, or Firm* — Michael L. Smith

(57) ABSTRACT

A method and an apparatus for extrapolating diagnostic data relating to one pupil diameter to another pupil diameter. Embodiments according to the invention are more particularly directed to extrapolating wavefront aberration data, for example, in the form of Zernike polynomial data, obtained from a smaller pupil diameter, $d_1$, to a larger pupil diameter, $d_2$. Data relating to the first pupil diameter $d_1$ may be obtained in a diagnostic procedure. In the extrapolation, a conversion matrix M is utilized. The conversion matrix M can be generated from a static matrix and a dynamic matrix, the latter taking the pupil diameter d1 into consideration. Data relating the first pupil diameter d1 and wavefront aberration data can be ordered via a permutation matrix P. If necessary, Extrapolated data can be re-ordered via a transposed permutation matrix $P^T$. The extrapolated data relating to the pupil diameter $d_2$ can be processed to obtain an ablation profile, a shot file, or other data for a refractive vision correction treatment.

8 Claims, 7 Drawing Sheets

| Zernike - Notification | Sight Defect | B&L - Notification |
|---|---|---|
| $Z_2^0$ | defocus | Z200 |
| $Z_2^2$ | 0° astigmatism | Z220 |
| $Z_2^{-2}$ | 45° astigmatism | Z221 |
| $Z_3^1$ | horizontal coma | Z310 |
| $Z_3^{-1}$ | vertical coma | Z311 |
| $Z_3^3$ | horizontal trefoil | Z330 |
| $Z_3^{-3}$ | vertical trefoil | Z331 |
| $Z_4^0$ | spherical aberration | Z400 |
| $Z_4^2$ | secondary 0° astigmatism | Z420 |
| $Z_4^{-2}$ | secondary 45° astigmatism | Z421 |
| $Z_4^4$ | horizontal quatrofoil | Z440 |
| $Z_4^{-4}$ | vertical quatrofoil | Z441 |
| $Z_5^1$ | secondary horizontal coma | Z510 |
| $Z_5^{-1}$ | secondary vertical coma | Z511 |
| $Z_5^3$ | secondary horizontal trefoil | Z530 |
| $Z_5^{-3}$ | secondary vertical trefoil | Z531 |
| $Z_5^5$ | horizontal pentafoil | Z550 |
| $Z_5^{-5}$ | vertical pentafoil | Z551 |

Figure 4b

| $S_{ij}$ | 200 | 221 | 220 | 311 | 310 | 331 | 330 | 400 | 421 | 420 | 441 | 440 | 511 | 510 | 531 | 530 | 551 | 550 |
|---|---|---|---|---|---|---|---|---|---|---|---|---|---|---|---|---|---|---|
| 200 | 1.212 | 0 | 0 | 0 | 0 | 0 | 0 | 1,216 | 0 | 0 | 0 | 0 | 0 | 0 | 0 | 0 | 0 | 0 |
| 221 | 0 | 1,212 | 0 | 0 | 0 | 0 | 0 | 0 | 0.139 | 0 | 0 | 0 | 0 | 0 | 0 | 0 | 0 | 0 |
| 220 | 0 | 0 | 1,212 | 0 | 0 | 0 | 0 | 0 | 0 | 0.139 | 0 | 0 | 0 | 0 | 0 | 0 | 0 | 0 |
| 311 | 0 | 0 | 0 | 1.127 | 0 | 0 | 0 | 0 | 0 | 0 | 0 | 0 | -0.827 | 0 | -0.108 | 0 | -0.108 | 0 |
| 310 | 0 | 0 | 0 | 0 | 1.127 | 0 | 0 | 0 | 0 | 0 | 0 | 0 | 0 | -0.827 | 0 | -0.108 | 0 | -0.108 |
| 331 | 0 | 0 | 0 | 0 | 0 | 1.127 | 0 | 0 | 0 | 0 | 0 | 0 | -0.108 | 0 | -1.208 | 0 | -0.108 | 0 |
| 330 | 0 | 0 | 0 | 0 | 0 | 0 | 1.127 | 0 | 0 | 0 | 0 | 0 | 0 | -0.108 | 0 | -1.208 | 0 | -0.108 |
| 400 | 0 | 0 | 0 | 0 | 0 | 0 | 0 | 1.446 | 0 | 0 | 0 | 0 | 0 | 0 | 0 | 0 | 0 | 0 |
| 421 | 0 | 0 | 0 | 0 | 0 | 0 | 0 | 0 | 0.281 | 0 | 0 | 0 | 0 | 0 | 0 | 0 | 0 | 0 |
| 420 | 0 | 0 | 0 | 0 | 0 | 0 | 0 | 0 | 0 | 0.281 | 0 | 0 | 0 | 0 | 0 | 0 | 0 | 0 |
| 441 | 0 | 0 | 0 | 0 | 0 | 0 | 0 | 0 | 0 | 0 | 0.031 | 0 | 0 | 0 | 0 | 0 | 0 | 0 |
| 440 | 0 | 0 | 0 | 0 | 0 | 0 | 0 | 0 | 0 | 0 | 0 | 0.031 | 0 | 0 | 0 | 0 | 0 | 0 |
| 511 | 0 | 0 | 0 | 0 | 0 | 0 | 0 | 0 | 0 | 0 | 0 | 0 | -1.017 | 0 | 0 | 0 | 0 | 0 |
| 510 | 0 | 0 | 0 | 0 | 0 | 0 | 0 | 0 | 0 | 0 | 0 | 0 | 0 | -1.017 | 0 | 0 | 0 | 0 |
| 531 | 0 | 0 | 0 | 0 | 0 | 0 | 0 | 0 | 0 | 0 | 0 | 0 | 0 | 0 | -0.825 | 0 | 0 | 0 |
| 530 | 0 | 0 | 0 | 0 | 0 | 0 | 0 | 0 | 0 | 0 | 0 | 0 | 0 | 0 | 0 | -0.825 | 0 | 0 |
| 551 | 0 | 0 | 0 | 0 | 0 | 0 | 0 | 0 | 0 | 0 | 0 | 0 | 0 | 0 | 0 | 0 | -1.088 | 0 |
| 550 | 0 | 0 | 0 | 0 | 0 | 0 | 0 | 0 | 0 | 0 | 0 | 0 | 0 | 0 | 0 | 0 | 0 | -1.088 |

| Dij | 200 | 221 | 220 | 311 | 310 | 331 | 330 | 400 | 421 | 420 | 441 | 440 | 511 | 510 | 531 | 530 | 551 | 550 |
|---|---|---|---|---|---|---|---|---|---|---|---|---|---|---|---|---|---|---|
| 200 | 0 | 0 | 0 | 0 | 0 | 0 | 0 | -0.039 | 0 | 0 | 0 | 0 | 0 | 0 | 0 | 0 | 0 | 0 |
| 221 | 0 | 0 | 0 | 0 | 0 | 0 | 0 | 0 | 0.12 | 0 | 0 | 0 | 0 | 0 | 0 | 0 | 0 | 0 |
| 220 | 0 | 0 | 0 | 0 | 0 | 0 | 0 | 0 | 0 | 0.12 | 0 | 0 | 0 | 0 | 0 | 0 | 0 | 0 |
| 311 | 0 | 0 | 0 | 0.033 | 0 | 0 | 0 | 0 | 0 | 0 | 0 | 0 | 0.295 | 0 | 0.014 | 0 | 0.014 | 0 |
| 310 | 0 | 0 | 0 | 0 | 0.033 | 0 | 0 | 0 | 0 | 0 | 0 | 0 | 0 | 0.295 | 0 | 0.014 | 0 | 0.014 |
| 331 | 0 | 0 | 0 | 0 | 0 | 0.033 | 0 | 0 | 0 | 0 | 0 | 0 | 0.014 | 0 | 0.353 | 0 | 0.014 | 0 |
| 330 | 0 | 0 | 0 | 0 | 0 | 0 | 0.033 | 0 | 0 | 0 | 0 | 0 | 0 | 0.014 | 0 | 0.353 | 0 | 0.014 |
| 400 | 0 | 0 | 0 | 0 | 0 | 0 | 0 | 0 | 0 | 0 | 0 | 0 | 0 | 0 | 0 | 0 | 0 | 0 |
| 421 | 0 | 0 | 0 | 0 | 0 | 0 | 0 | 0 | 0.168 | 0 | 0 | 0 | 0 | 0 | 0 | 0 | 0 | 0 |
| 420 | 0 | 0 | 0 | 0 | 0 | 0 | 0 | 0 | 0 | 0.168 | 0 | 0 | 0 | 0 | 0 | 0 | 0 | 0 |
| 441 | 0 | 0 | 0 | 0 | 0 | 0 | 0 | 0 | 0 | 0 | 0.199 | 0 | 0 | 0 | 0 | 0 | 0 | 0 |
| 440 | 0 | 0 | 0 | 0 | 0 | 0 | 0 | 0 | 0 | 0 | 0 | 0.199 | 0 | 0 | 0 | 0 | 0 | 0 |
| 511 | 0 | 0 | 0 | 0 | 0 | 0 | 0 | 0 | 0 | 0 | 0 | 0 | 0.359 | 0 | 0 | 0 | 0 | 0 |
| 510 | 0 | 0 | 0 | 0 | 0 | 0 | 0 | 0 | 0 | 0 | 0 | 0 | 0 | 0.359 | 0 | 0 | 0 | 0 |
| 531 | 0 | 0 | 0 | 0 | 0 | 0 | 0 | 0 | 0 | 0 | 0 | 0 | 0 | 0 | 0.329 | 0 | 0 | 0 |
| 530 | 0 | 0 | 0 | 0 | 0 | 0 | 0 | 0 | 0 | 0 | 0 | 0 | 0 | 0 | 0 | 0.329 | 0 | 0 |
| 551 | 0 | 0 | 0 | 0 | 0 | 0 | 0 | 0 | 0 | 0 | 0 | 0 | 0 | 0 | 0 | 0 | 0.37 | 0 |
| 550 | 0 | 0 | 0 | 0 | 0 | 0 | 0 | 0 | 0 | 0 | 0 | 0 | 0 | 0 | 0 | 0 | 0 | 0.37 |

Figure 8

| NbDiyj | 200 | 220 | 221 | 310 | 311 | 330 | 331 | 400 | 420 | 421 | 440 | 441 | 510 | 511 | 530 | 531 | 550 | 551 |
|---|---|---|---|---|---|---|---|---|---|---|---|---|---|---|---|---|---|---|
| Z200 | 1,212 | 0 | 0 | 0 | 0 | 0 | 0 | 1,021 | 0 | 0 | 0 | 0 | 0 | 0 | 0 | 0 | 0 | 0 |
| Z220 | 0 | 1,212 | 0 | 0 | 0 | 0 | 0 | 0 | 0,739 | 0 | 0 | 0 | 0 | 0 | 0 | 0 | 0 | 0 |
| Z221 | 0 | 0 | 1,212 | 0 | 0 | 0 | 0 | 0 | 0 | 0,739 | 0 | 0 | 0 | 0 | 0 | 0 | 0 | 0 |
| Z310 | 0 | 0 | 0 | 1,292 | 0 | 0 | 0 | 0 | 0 | 0 | 0 | 0 | 0,648 | 0 | -0,038 | 0 | -0,038 | 0 |
| Z311 | 0 | 0 | 0 | 0 | 1,292 | 0 | 0 | 0 | 0 | 0 | 0 | 0 | 0 | 0,648 | 0 | -0,038 | 0 | -0,038 |
| Z330 | 0 | 0 | 0 | 0 | 0 | 1,292 | 0 | 0 | 0 | 0 | 0 | 0 | -0,038 | 0 | 0,559 | 0 | -0,038 | 0 |
| Z331 | 0 | 0 | 0 | 0 | 0 | 0 | 1,292 | 0 | 0 | 0 | 0 | 0 | 0 | -0,038 | 0 | 0,559 | 0 | -0,038 |
| Z400 | 0 | 0 | 0 | 0 | 0 | 0 | 0 | 1,446 | 0 | 0 | 0 | 0 | 0 | 0 | 0 | 0 | 0 | 0 |
| Z420 | 0 | 0 | 0 | 0 | 0 | 0 | 0 | 0 | 1,121 | 0 | 0 | 0 | 0 | 0 | 0 | 0 | 0 | 0 |
| Z421 | 0 | 0 | 0 | 0 | 0 | 0 | 0 | 0 | 0 | 1,121 | 0 | 0 | 0 | 0 | 0 | 0 | 0 | 0 |
| Z440 | 0 | 0 | 0 | 0 | 0 | 0 | 0 | 0 | 0 | 0 | 1,026 | 0 | 0 | 0 | 0 | 0 | 0 | 0 |
| Z441 | 0 | 0 | 0 | 0 | 0 | 0 | 0 | 0 | 0 | 0 | 0 | 1,026 | 0 | 0 | 0 | 0 | 0 | 0 |
| Z510 | 0 | 0 | 0 | 0 | 0 | 0 | 0 | 0 | 0 | 0 | 0 | 0 | 0,778 | 0 | 0 | 0 | 0 | 0 |
| Z511 | 0 | 0 | 0 | 0 | 0 | 0 | 0 | 0 | 0 | 0 | 0 | 0 | 0 | 0,778 | 0 | 0 | 0 | 0 |
| Z530 | 0 | 0 | 0 | 0 | 0 | 0 | 0 | 0 | 0 | 0 | 0 | 0 | 0 | 0 | 0,82 | 0 | 0 | 0 |
| Z531 | 0 | 0 | 0 | 0 | 0 | 0 | 0 | 0 | 0 | 0 | 0 | 0 | 0 | 0 | 0 | 0,82 | 0 | 0 |
| Z550 | 0 | 0 | 0 | 0 | 0 | 0 | 0 | 0 | 0 | 0 | 0 | 0 | 0 | 0 | 0 | 0 | 0,762 | 0 |
| Z551 | 0 | 0 | 0 | 0 | 0 | 0 | 0 | 0 | 0 | 0 | 0 | 0 | 0 | 0 | 0 | 0 | 0 | 0,762 |

Figure 9

| NoDyj | 200 | 220 | 221 | 310 | 311 | 330 | 331 | 400 | 420 | 421 | 440 | 441 | 510 | 511 | 530 | 531 | 550 | 551 |
|---|---|---|---|---|---|---|---|---|---|---|---|---|---|---|---|---|---|---|
| Z200 | 1,212 | 0 | 0 | 0 | 0 | 0 | 0 | 0,982 | 0 | 0 | 0 | 0 | 0 | 0 | 0 | 0 | 0 | 0 |
| Z220 | 0 | 1,212 | 0 | 0 | 0 | 0 | 0 | 0 | 0,859 | 0 | 0 | 0 | 0 | 0 | 0 | 0 | 0 | 0 |
| Z221 | 0 | 0 | 1,212 | 0 | 0 | 0 | 0 | 0 | 0 | 0,859 | 0 | 0 | 0 | 0 | 0 | 0 | 0 | 0 |
| Z310 | 0 | 0 | 0 | 1,325 | 0 | 0 | 0 | 0 | 0 | 0 | 0 | 0 | 0,943 | 0 | -0,024 | 0 | -0,024 | 0 |
| Z311 | 0 | 0 | 0 | 0 | 1,325 | 0 | 0 | 0 | 0 | 0 | 0 | 0 | 0 | 0,943 | 0 | -0,024 | 0 | -0,024 |
| Z330 | 0 | 0 | 0 | 0 | 0 | 1,325 | 0 | 0 | 0 | 0 | 0 | -0,024 | 0 | 0,912 | 0 | -0,024 | 0 |
| Z331 | 0 | 0 | 0 | 0 | 0 | 0 | 1,325 | 0 | 0 | 0 | 0 | 0 | -0,024 | 0 | 0,912 | 0 | -0,024 |
| Z400 | 0 | 0 | 0 | 0 | 0 | 0 | 0 | 1,446 | 0 | 0 | 0 | 0 | 0 | 0 | 0 | 0 | 0 | 0 |
| Z420 | 0 | 0 | 0 | 0 | 0 | 0 | 0 | 0 | 1,289 | 0 | 0 | 0 | 0 | 0 | 0 | 0 | 0 | 0 |
| Z421 | 0 | 0 | 0 | 0 | 0 | 0 | 0 | 0 | 0 | 1,289 | 0 | 0 | 0 | 0 | 0 | 0 | 0 | 0 |
| Z440 | 0 | 0 | 0 | 0 | 0 | 0 | 0 | 0 | 0 | 0 | 1,225 | 0 | 0 | 0 | 0 | 0 | 0 | 0 |
| Z441 | 0 | 0 | 0 | 0 | 0 | 0 | 0 | 0 | 0 | 0 | 0 | 1,225 | 0 | 0 | 0 | 0 | 0 | 0 |
| Z510 | 0 | 0 | 0 | 0 | 0 | 0 | 0 | 0 | 0 | 0 | 0 | 0 | 1,137 | 0 | 0 | 0 | 0 | 0 |
| Z511 | 0 | 0 | 0 | 0 | 0 | 0 | 0 | 0 | 0 | 0 | 0 | 0 | 0 | 1,137 | 0 | 0 | 0 | 0 |
| Z530 | 0 | 0 | 0 | 0 | 0 | 0 | 0 | 0 | 0 | 0 | 0 | 0 | 0 | 0 | 1,149 | 0 | 0 | 0 |
| Z531 | 0 | 0 | 0 | 0 | 0 | 0 | 0 | 0 | 0 | 0 | 0 | 0 | 0 | 0 | 0 | 1,149 | 0 | 0 |
| Z550 | 0 | 0 | 0 | 0 | 0 | 0 | 0 | 0 | 0 | 0 | 0 | 0 | 0 | 0 | 0 | 0 | 1,132 | 0 |
| Z551 | 0 | 0 | 0 | 0 | 0 | 0 | 0 | 0 | 0 | 0 | 0 | 0 | 0 | 0 | 0 | 0 | 0 | 1,132 |

Figure 10

| NoDyj | 200 | 220 | 221 | 310 | 311 | 330 | 331 | 400 | 420 | 421 | 440 | 441 | 510 | 511 | 530 | 531 | 550 | 551 |
|---|---|---|---|---|---|---|---|---|---|---|---|---|---|---|---|---|---|---|
| Z200 | 1,212 | 0 | 0 | 0 | 0 | 0 | 0 | 0,943 | 0 | 0 | 0 | 0 | 0 | 0 | 0 | 0 | 0 | 0 |
| Z220 | 0 | 1,212 | 0 | 0 | 0 | 0 | 0 | 0 | 0,979 | 0 | 0 | 0 | 0 | 0 | 0 | 0 | 0 | 0 |
| Z221 | 0 | 0 | 1,212 | 0 | 0 | 0 | 0 | 0 | 0 | 0,979 | 0 | 0 | 0 | 0 | 0 | 0 | 0 | 0 |
| Z310 | 0 | 0 | 0 | 1,368 | 0 | 0 | 0 | 0 | 0 | 0 | 0 | 0 | 1,238 | 0 | -0,01 | 0 | -0,01 | 0 |
| Z311 | 0 | 0 | 0 | 0 | 1,368 | 0 | 0 | 0 | 0 | 0 | 0 | 0 | 0 | 1,238 | 0 | -0,01 | 0 | -0,01 |
| Z330 | 0 | 0 | 0 | 0 | 0 | 1,368 | 0 | 0 | 0 | 0 | 0 | -0,01 | 0 | 1,265 | 0 | -0,01 | 0 |
| Z331 | 0 | 0 | 0 | 0 | 0 | 0 | 1,368 | 0 | 0 | 0 | 0 | 0 | -0,01 | 0 | 1,265 | 0 | -0,01 |
| Z400 | 0 | 0 | 0 | 0 | 0 | 0 | 0 | 1,446 | 0 | 0 | 0 | 0 | 0 | 0 | 0 | 0 | 0 | 0 |
| Z420 | 0 | 0 | 0 | 0 | 0 | 0 | 0 | 0 | 1,457 | 0 | 0 | 0 | 0 | 0 | 0 | 0 | 0 | 0 |
| Z421 | 0 | 0 | 0 | 0 | 0 | 0 | 0 | 0 | 0 | 1,457 | 0 | 0 | 0 | 0 | 0 | 0 | 0 | 0 |
| Z440 | 0 | 0 | 0 | 0 | 0 | 0 | 0 | 0 | 0 | 0 | 1,424 | 0 | 0 | 0 | 0 | 0 | 0 | 0 |
| Z441 | 0 | 0 | 0 | 0 | 0 | 0 | 0 | 0 | 0 | 0 | 0 | 1,424 | 0 | 0 | 0 | 0 | 0 | 0 |
| Z510 | 0 | 0 | 0 | 0 | 0 | 0 | 0 | 0 | 0 | 0 | 0 | 0 | 1,496 | 0 | 0 | 0 | 0 | 0 |
| Z511 | 0 | 0 | 0 | 0 | 0 | 0 | 0 | 0 | 0 | 0 | 0 | 0 | 0 | 1,496 | 0 | 0 | 0 | 0 |
| Z530 | 0 | 0 | 0 | 0 | 0 | 0 | 0 | 0 | 0 | 0 | 0 | 0 | 0 | 0 | 1,478 | 0 | 0 | 0 |
| Z531 | 0 | 0 | 0 | 0 | 0 | 0 | 0 | 0 | 0 | 0 | 0 | 0 | 0 | 0 | 0 | 1,478 | 0 | 0 |
| Z550 | 0 | 0 | 0 | 0 | 0 | 0 | 0 | 0 | 0 | 0 | 0 | 0 | 0 | 0 | 0 | 0 | 1,502 | 0 |
| Z551 | 0 | 0 | 0 | 0 | 0 | 0 | 0 | 0 | 0 | 0 | 0 | 0 | 0 | 0 | 0 | 0 | 0 | 1,502 |

Figure 11

METHOD AND APPARATUS FOR EXTRAPOLATING DIAGNOSTIC DATA

FIELD OF THE INVENTION

Embodiments of the present invention relate to the field of ophthalmic wavefront driven procedures and, particularly, to a method and an apparatus for extrapolating diagnostic data relating to one pupil diameter to another pupil diameter; and more specifically for extrapolating of wavefront aberration data.

BACKGROUND OF THE INVENTION

In the past various improvements have been made in the field of refractive vision correction treatments. In many cases these treatments rely upon data obtained in a diagnostic procedure wherein the wavefront aberration and/or topographic data, for example, of the eye are determined.

During the diagnostic examination of an eye, it is desirable for the eye to have a large pupil diameter. Therefore, it is common to use pharmacological pupil dilation to dilate the pupil. However, pharmacological pupil dilation has disadvantages.

Charles E. Campbell describes in the publication "Matrix method to find a new set of Zernike coefficients from an original set when the aperture radius is changed" (J. Opt. Soc. Am. A, February 2003, Vol. 20, No. 2, pages 209 to 217) to form a new set of Zernike coefficients arranged as elements of a vector by multiplying the original set of coefficients, also arranged as elements of a vector, by a conversion matrix formed from powers of the ratio of the new aperture to the original aperture and elements of a matrix that forms the weighting coefficients of the radial Zernike polynomial functions. The conversion matrix according to Campbell is determined corresponding to the extrapolation ratio. As disclosed therein, if the new aperture radius is larger than the original, then the portion of the new surface that lies within the original aperture boundary identically matches the original surface. However, for areas of the new aperture that lie outside the old aperture, the reference states that it is best to normalize by reducing the aperture size of the larger to that of the smaller aperture before making comparisons. Thus there is no disclosure teaching an applicable extrapolation for vision correction treatments.

SUMMARY OF THE INVENTION

Embodiments of the invention are directed to a method and an apparatus for extrapolating diagnostic data relating to a first pupil diameter to data relating to a second pupil diameter. More particularly, embodiments of the invention are directed to the extrapolation of wavefront aberration data obtained at a first pupil diameter d1, to a second, larger pupil diameter d2.

According to various aspects, a method and an apparatus are disclosed for providing data relating to a second pupil diameter d2 obtained from data relating to a first pupil diameter d1 by way of extrapolation, wherein the second pupil diameter d2 is larger than the first pupil diameter d1. The wavefront data relating to the first pupil diameter d1 are obtained in a diagnostic procedure as known in the art; for example, by using a Zywave™ aberrometer (Bausch & Lomb Incorporated, Rochester, N.Y.).

According to an aspect involving the extrapolation of data, a conversion matrix M is utilized, which corresponds to the first pupil diameter d1; i.e., the elements of the conversion matrix are different for each different first pupil diameter d1, even when there may be a constant extrapolation ratio. The conversion matrix M is generated from a static matrix and a dynamic matrix, the latter taking the pupil diameter d1 into consideration. The conversion matrix may further depend on the type of measured wavefront data, e.g., myopic, mixed astigmatism and/or, hyperopic.

The measured wavefront aberration data can be represented by Zernike polynomials, i.e., the wavefront information acquired can be represented by Zernike amplitudes. Both the measured Zernike amplitudes and the related pupil size d1 represent input data used to obtain the extrapolated wavefront data relating to a pupil diameter d2.

Prior to the data extrapolation, the data relating the first pupil diameter d1, which may be obtained in a prior measurement, and the wavefront aberration data such as represented by Zernike amplitudes, can be ordered in a certain way, e.g., via a permutation matrix P. In an aspect, the later obtained extrapolated data are re-ordered via a transposed permutation matrix $P^T$.

In another aspect, the extrapolated data relating to the pupil diameter d2 can be processed to obtain an ablation profile or other appropriate data for a refractive vision correction treatment. The treatment may be conducted immediately or otherwise after the diagnostic measurement and the appropriate data processing.

The objects and advantages of the presently embodied invention will become more readily apparent from the following detailed description. However, it should be understood that the detailed description and specific examples, while indicating particular embodiments of the invention, are given by way of illustration only. Various changes and modifications within the scope of the invention will be apparent to those skilled in the art based upon the description and drawings herein and the appended claims.

BRIEF DESCRIPTION OF THE DRAWINGS

FIG. 4b is a chart listing the Zernike polynomial notation, the respective aberration, and the corresponding Bausch & Lomb notation;

FIG. 8 shows an exemplary dynamic matrix D according to an embodiment of the invention;

FIG. 9 shows a conversion matrix M useful for extrapolating wavefront data from 5.0 mm to 5.5 mm according to an exemplary embodiment of the invention;

FIG. 10 shows a conversion matrix M for extrapolating wavefront data from 6.0 mm to 6.6 mm according to an exemplary embodiment of the invention; and FIG. 11 shows a conversion matrix M for extrapolating wavefront data from 7.0 mm to 7.7 mm according to an exemplary embodiment of the invention;

DETAILED DESCRIPTION OF EMBODIMENTS OF THE INVENTION

It is known by a person skilled in the art that pupil diameter changes as a function of the illumination level L and is classified as:

Scotopic, when (L<0.001 cd/m$^2$);
Mesopic, when (0.001 cd/m$^2$<L<3 cd/m$^2$); and
Photopic, when (L>3 cd/m$^2$).

For the purpose of performing a refractive vision correction treatment, it is desirable to obtain diagnostic data from an optical zone that is about 0.2 mm to 0.5 mm larger in diameter than that of the mesopic pupil. Thus, when performing a wavefront aberration measurement on a mesopic eye, which has a typical pupil size of about 5.5 mm in diameter, this measurement will not necessarily provide sufficient data.

Figure 1:
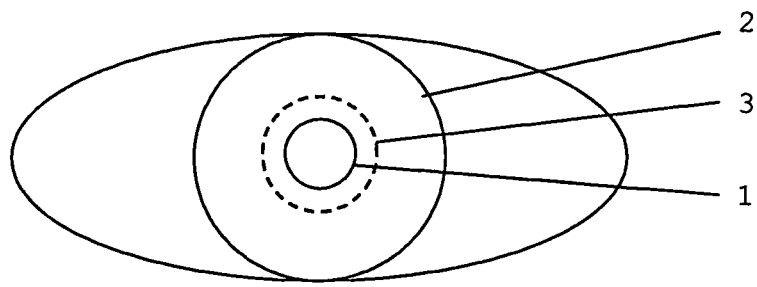
FIG. 1 schematically shows an eye having a pupil (solid inner circle) smaller than the optical zone (dotted line)

FIG. 1 schematically shows an eye 10 having an iris 2 with a pupil 1 under normal light conditions, wherein the mesopic pupil 1 is smaller than the optical zone 3 for which data are to be obtained. This additional data, i.e., in the region between the mesopic pupil and the optical zone, is desirable in order to determine an ablation profile that takes into account the periphery of the desired treatment zone. If the ablation profile does not cover the periphery, the patient may experience glare, halos, ghost images, or other visual defects in low illumination, i.e., when the patient's pupil is typically dilated.

Thus, it is particularly advantageous to obtain data for the eye within the entire optical zone 3 to help ensure a most successful vision correction outcome.

Two possible approaches to making the desired measurements are pharmacological pupil dilation and a mathematical extrapolation of measured eye data from a smaller pupil.

Figure 2:
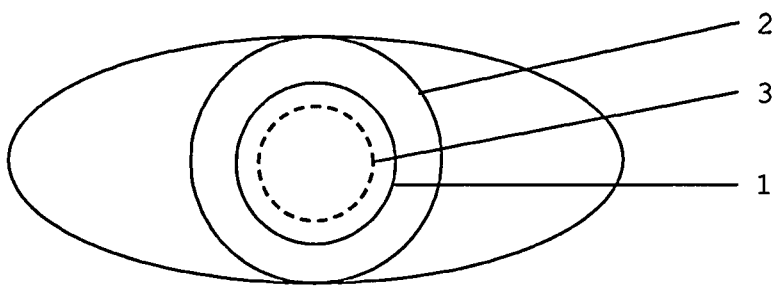
FIG. 2 schematically shows an eye having a pupil (solid inner circle) larger than the optical zone (dotted line)

In an aspect involving pharmacological pupil dilation, which is shown in FIG. 2, drops are applied into the eye 10 to be measured. After a certain period of time, typically about 10 minutes, the pupil 1 fully dilates, even extending beyond its normal size under scotopic conditions. A diagnostic measurement can now be conducted to obtain data within the optical zone 3.

After pharmacological pupil dilation, the pupil 1 will constrict to its normal diameter, after which the treatment can be conducted. Thus a vision correction treatment is typically performed about one day after the diagnostic procedure.

A further disadvantage associated with pharmacological pupil dilation is the fact that the pupil center may shift with increasing dilation of the pupil. This center shift effect is not shown in FIG. 2. As explained above, the pupil dilates beyond scotopic conditions and thus a noticeable measurement error can occur. For instance, if the measurement of the eye is obtained from a large pupil with a shifted center and the vision correction treatment is centered over the pupil of small diameter, an error in the treatment procedure may occur.

Figure 4A:
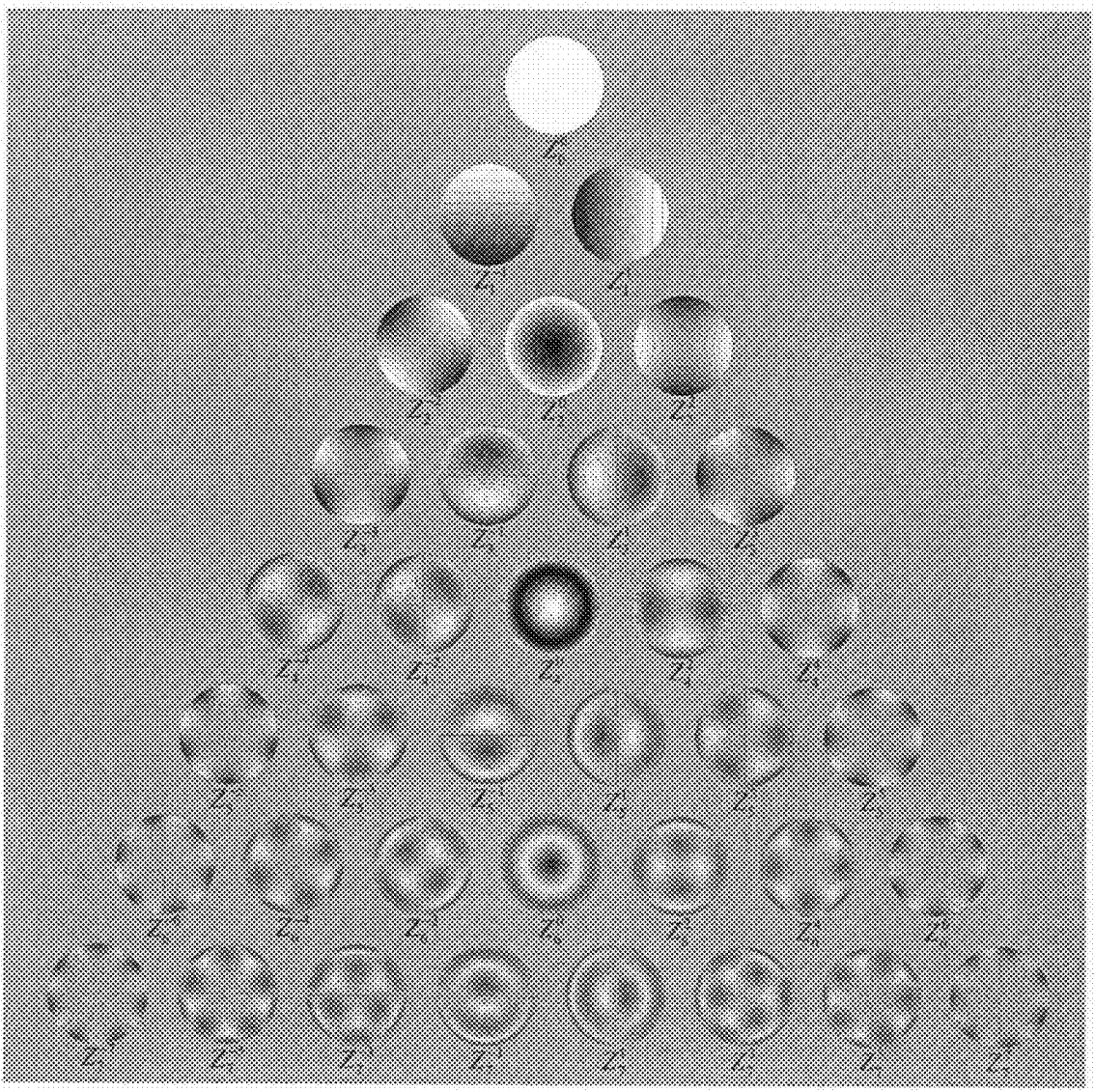
FIG. 4a shows a density plot of the Zernike polynomials up to the seventh order.

Mathematical attempts to extrapolate wavefront aberration data represent another technique. A brief introduction to the basic principles of Zernike polynomials will be given in connection with FIG. 4a, which shows a density plot of Zernike polynomials up to the seventh order. FIG. 4b provides a list of the Zernike polynomials, their respective vision defects, and the Bausch & Lomb notation, which is utilized in the matrices as shown in FIGS. 7 to 10. The list according to FIG. 4b shows the Zernike polynomials from the second order (Z2xx) up to the fifth order (Z5xx).

Wavefront aberration can be represented by Zernike polynomials and their respective amplitudes. These polynomials are used in optical sciences for many reasons. The Zernike polynomials are defined on a unit circle, which applies to most of the optical problems that deal with circular system apertures. The Zernike polynomials represent a system of orthogonal functions, so a huge variety of optical and mathematical problems can be solved by using mathematical expansion and de-convolution techniques.

The amplitudes A of Zernike polynomials can be represented mathematically as follows.

$$A_{n,m}{}^\pi$$

where n represents the Zernike mode, which is the primary parameter in the classification of the radial behavior of the polynomial. The angular characteristic of the polynomial is specified by the parameter m, which describes how often a certain structure is repeated in azimuthal direction. The larger the value for m, the more sophisticated or complicated will be the azimuthal profile of the polynomial. The parameter $\pi$ describes the symmetry characteristic of the polynomial, i.e., even or odd.

Reference is made to FIG. 4a which illustrates the behavior of the above discussed parameters, whereas the OSA standard notation (Thibos et. al., 2000) as used in FIGS. 4a and 4b for the Zernike polynomials Z is defined as follows:

$$Z_n{}^{\pi \cdot m}$$

The original wavefront error W of the eye can be reconstructed by a linear combination of the calculated Zernike polynomials Z, taking into account their individual amplitudes $A_{n,m}{}^\pi$ using the following equation:

$$W(\rho, \varphi) = \sum_{n,m,\pi} A_{n,m}^\pi \times Z_{n,m}^\pi(\rho, \varphi)$$

The notation $Z_{n,m}{}^\pi$ corresponds to $Z_n{}^{\pi \cdot m}$ of the OSA standard notation. The parameters $\rho, \phi$ represent the coordinate values.

Extending these polynomials beyond the normalized pupil or the unit circle, however, may not guarantee that the results describe the reality of wavefront aberrations outside the original pupil size.

As a first step the measurement results relating to a certain pupil diameter are normalized, e.g., if a measurement of an eye with a maximum pupil radius of 2.5 mm is obtained, this 2.5 mm equals 1 in the unit circle.

The only information available for any kind of extrapolation are the individually determined Zernike coefficients in the diagnostic procedure relating to the original system aperture. This information is used to expand the model for the wavefront aberrations of the system, described in Zernike polynomials.

It is an object according to the embodiments of the invention to extrapolate the data, i.e., to calculate wavefront aberration data beyond the border of the unit circle. There are two principal techniques disclosed to achieve this object.

One technique is to assume that the actual pupil was larger when the measurement was performed, and push the border to the desired diameter. With increasing enlargement of the border, the measured function is flattened. While data outside of the original pupil diameter have been generated, the wavefront shape inside the pupil is modified. As a result, the new generated data may not necessarily be correct.

Another attempt is to ignore the unit circle criterion and move beyond the border. Thus, data within the border remain unchanged, however, data relating to outside of the border do not make sense. This is a result of the Zernike polynomials which are only defined within the unit circle as described above.

Summing In any event, the above described mathematical tools for extrapolating the wavefront do not provide feasible results.

Figure 3:
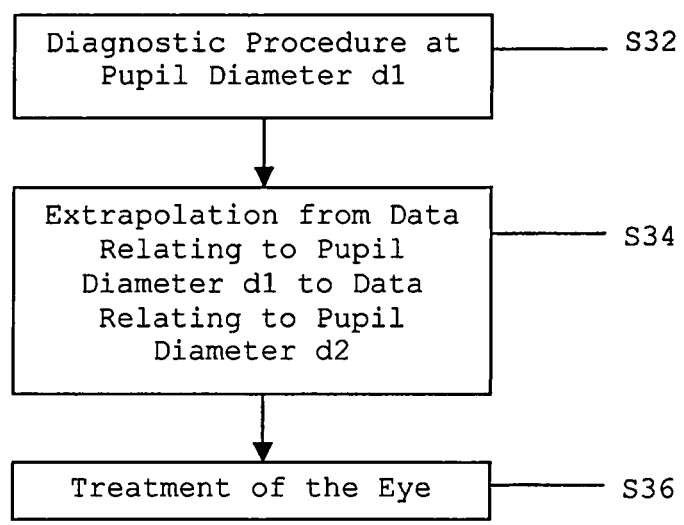
FIG. 3 shows a flow chart of the steps from diagnosis to vision correction treatment according to an embodiment of the invention.

As shown in diagram 300 at step S32 in FIG. 3, data of an eye to be treated are obtained. Diagnostic data, in particular wavefront measurement data, are acquired for a first pupil diameter $d_1$. Pharmacological dilation is not used so that the above explained shortfalls can be avoided.

The eye is measured having a pupil diameter d1, which is smaller than the diameter of the optical zone, for which it is desirable to obtain data for a later vision correction treatment. In order to obtain diagnostic data relating to a pupil diameter d2, which is larger than the pupil diameter d1 and, at least as large as the optical zone, the data as measured in step S32 are extrapolated in step S34. The input data for the extrapolation are at least the wavefront aberration data, the pupil diameter d1 during the measurement of the wavefront aberration data and the desired extrapolation ratio. The wavefront aberration data can be provided in the form of Zernike coefficients, e.g., in the form of a vector. The extrapolation ratio can be selected as any value in a range of 1% to 30%, e.g., 1%, 5%, 10%, 15%, 20%, 25% or 30%. The extrapolation ratio can also be determined on a dynamic basis, i.e., to extrapolate the respective data to such an extent as to provide wavefront aberration data covering at least the optical zone of an eye. Thus, if an eye is measured having a pupil diameter of 6.4 mm and the desired measurement diameter is 7 mm, the extrapolation ratio would be determined to be 10%, thereby producing at least the data for the desired pupil diameter, i.e., to obtain data covering at least the optical zone.

The above obtained data may be utilized in a later step S36 for a vision correction treatment, whereas several intermediate steps may be performed to obtain other data, e.g., a laser shot file.

Figure 5:
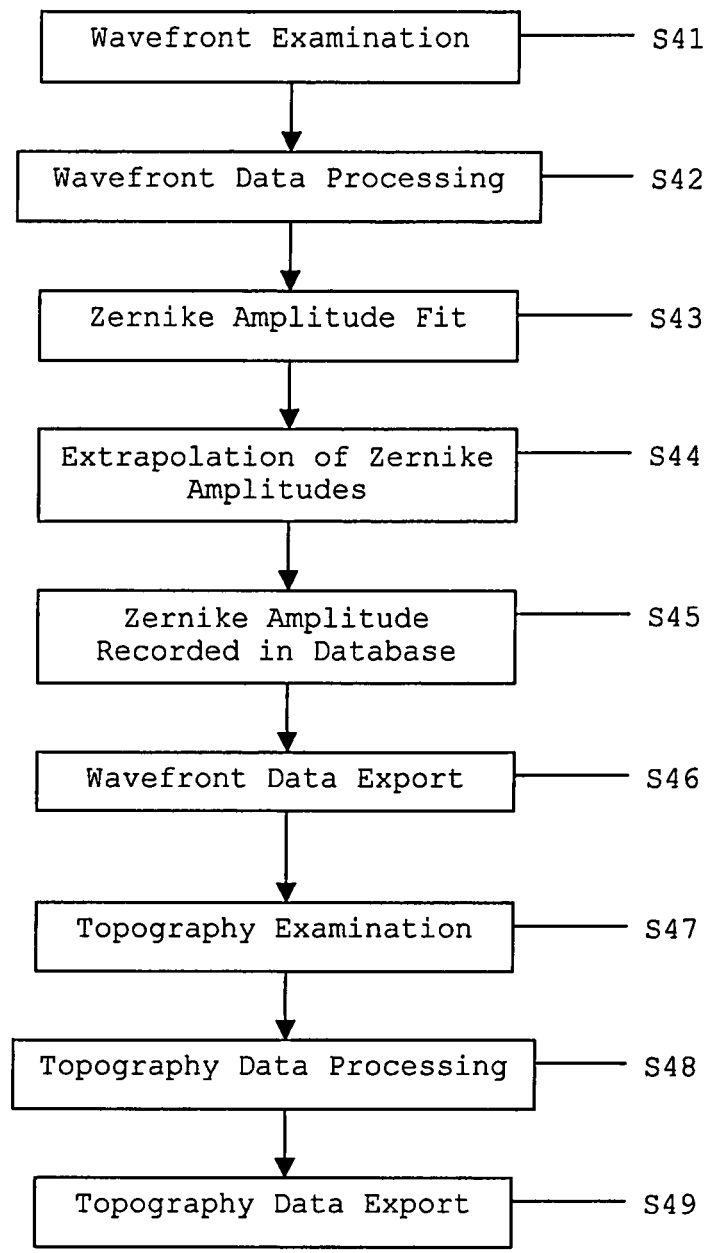
FIG. 5 shows a flow chart relating to a diagnostic procedure according to an embodiment of the invention.

FIG. 5 provides a more detailed flow chart 500 relating to the diagnostic procedure as described in step S32 above. In step S41, the wavefront of an eye is examined. One suitable way to obtain the wavefront data is with a Hartmann-Shack wave-front sensor. In this measurement the wave aberrations of the human eye are sensed by the wave front emerging from the eye produced by the retinal reflection of a focused light spot on the fovea. In step S42, the obtained data is further processed and the wave front can be reconstructed by the use of wave-front estimation with Zernike polynomials, which is done in step S43. The wavefront of the examined eye is represented by Zernike amplitudes, as is well understood in the art.

For further information regarding the Hartmann-Shack wave-front sensor the reader is referred to "Objective measurement of wave aberrations of the human eye with the use of a Hartmann-Shack wave-front sensor" from Junzhong Liang et al. (J. Opt. Soc. Am. A, July 1994, Vol. 11, No. 7, pages 1949 to 1957), the subject matter of which is herein incorporated by reference in its entirety.

In step S44, the Zernike coefficients relating to a first pupil diameter $d_1$ are extrapolated to obtain Zernike coefficients relating to a second pupil diameter d2, where the second pupil diameter is larger than the first pupil diameter. In step S45, the obtained coefficients can be recorded in database and/or exported in step S46 for further data processing, e.g., calculation of a laser shot profile.

According to an optional feature of the invention in a subsequent step S47, topographic data are obtained during a respective examination. The topographic data are processed in step S48 and exported in step S49.

Step S44, i.e., the extrapolation of Zernike coefficients, will be described in more detail below.

A vector Z1 containing wavefront aberration data relating to the first pupil diameter d1 is multiplied with a conversion matrix M to obtain a vector Z2 containing Zernike coefficients relating to the second pupil diameter.

$$Z2_i = \sum_{j=1}^{18} M_{i,j} \times Z1_j$$

This leads to the following exemplary equation containing a total number of 18 Zernike modes:

$$\begin{pmatrix} Z2_1 \\ \vdots \\ Z2_{18} \end{pmatrix} = \begin{pmatrix} M_{1;1} & \cdots & M_{1;18} \\ \vdots & \ddots & \vdots \\ M_{18;1} & \cdots & M_{18;18} \end{pmatrix} \otimes \begin{pmatrix} Z1_1 \\ \vdots \\ Z1_{18} \end{pmatrix}$$

However, the number of Zernike modes may be varied to any number, i.e., it may be greater or smaller.

In the latter equation the values $Z1_1$ to $Z1_{18}$ represent the Zernike coefficients relating to the first pupil diameter d1. The values $Z2_1$ to $Z2_{18}$ represent the Zernike coefficients relating to the second pupil diameter d2, i.e., the extrapolated data.

In an optional step the Zernike coefficients $Z1_1$ to $Z1_{18}$ relating to the first pupil diameter d1 are ordered in the vector Z1 in an appropriate order, e.g., via a permutation matrix P. The Zernike coefficients $Z2_1$ to $Z2_{18}$ in the vector Z2 may be reordered, e.g., using a transposed permutation matrix $P^T$.

In a further optional step the Zernike coefficients $Z1_1$ to $Z1_{18}$ relating to the first pupil diameter d1 can be converted to a non-normalized form, in the event the coefficients are given in normalized form. After the new set of coefficients $Z2_1$ to $Z2_{18}$ is formed, it may be converted back to normalized form for further processing.

It is noted that different conversion matrices M may be utilized depending on the ametropia, i.e., the matrix elements and/or its value vary depending on the vision error of the eye, e.g., myopia, hyperopia, astigmatism and combinations thereof.

For different extrapolation ratios, different conversion matrices M are utilized.

The conversion matrix M is the sum of a static matrix S and a dynamic matrix D, wherein the dynamic matrix is multiplied with the first pupil diameter d1, thereby incorporating the pupil diameter d1 into the conversion matrix M.

$$M_{i,j}(d1) = S_{i,j}^0 + d1 \times D_{i,j}$$

The conversion matrix M, e.g., takes the cross influences of different Zernike modes into consideration. This will be discussed in more detail in the following.

The extrapolated Zernike coefficient representing the defocus value of the pupil diameter d2 is based on a weighted defocus value relating to the first pupil diameter d1 and, optionally, a weighted spherical aberration value relating to the first pupil diameter d1. In particular, the defocus value relating to the first pupil diameter d1 is multiplied with a factor $M_{1;1}$ and, the optional spherical aberration value relating to the first pupil diameter d1 is multiplied with a factor $M_{1;8}$. The factor $M_{1;8}$ may decrease with increasing pupil diameter d1.

$$Z2_{defocus} = M(d1)_{1;1} \times Z1_{defocus} + M(d1)_{1;8} \times Z1_{spherical\_aberration}$$

The extrapolated Zernike coefficient representing the 0° astigmatism value of the extrapolated pupil diameter d2 is based on a 0° weighted astigmatism value relating to the first pupil diameter d1 and, optionally, on a weighted secondary 0° astigmatism value relating to the first pupil diameter d1. In particular, the 0° astigmatism value relating to the first pupil diameter d1 is multiplied with a factor $M_{2;2}$ and, the optional secondary 0° astigmatism value relating to the first pupil diameter d1 is multiplied with a factor $M_{2;9}$. The factor $M_{2;9}$ may increase with increasing pupil diameter d1.

$$Z2_{0°astigmatism} = M(d1)_{2;2} \times Z1_{0°astigmatism} + M(d1)_{2;9} \times Z1_{secondary\_0°astigmatism}$$

The extrapolated Zernike coefficient representing the 45° astigmatism value of the extrapolated pupil diameter d2 is based on a weighted 45° astigmatism value relating to the first pupil diameter d1 and, optionally, on a weighted secondary 45° astigmatism value relating to the first pupil diameter d1. In particular, the 45° astigmatism value relating to the first pupil diameter d1 is multiplied with a factor $M_{3;3}$ and, the optional secondary 45° astigmatism value relating to the first pupil diameter d1 is multiplied with a factor $M_{3;10}$. The factor $M_{3;10}$ may increase with increasing pupil diameter d1.

$$Z2_{45°astigmatism} = M(d1)_{3;3} \times Z1_{45°astigmatism} + M(d1)_{3;10} \times Z_{secondary\_45°astigmatism}$$

The extrapolated Zernike coefficient representing the horizontal coma value of the extrapolated pupil diameter d2 is based on a weighted horizontal coma value relating to the first pupil diameter d1 and, optionally, on a secondary horizontal coma value relating to the first pupil diameter d1. In particular, the horizontal coma value relating to the first pupil diameter d1 is multiplied with a factor $M_{4;4}$ and, the optional secondary horizontal coma value relating to the first pupil diameter d1 is multiplied with a factor $M_{4;13}$. The factor $M_{4;13}$ may increase with increasing pupil diameter d1.

The extrapolated Zernike coefficient representing the horizontal coma value of the extrapolated pupil diameter d2 is, optionally, further based on a weighted secondary horizontal trefoil value relating to the first pupil diameter d1. In particular, the optional secondary horizontal trefoil value relating to the first pupil diameter d1 is multiplied with a factor $M_{4;15}$. The factor $M_{4;15}$ may increase with increasing pupil diameter d1.

The extrapolated Zernike coefficient representing the horizontal coma value of the extrapolated pupil diameter d2 is, optionally, further based on a weighted horizontal pentafoil value relating to the first pupil diameter d1. In particular, the optional horizontal pentafoil value relating to the first pupil diameter d1 is multiplied with a factor $M_{4;17}$. The factor $M_{4;17}$ may increase with increasing pupil diameter d1.

$$Z2_{horizontal\_coma} = M(d1)_{4;4} \times Z1_{horizontal\_coma} + M(d1)_{4;13} \times Z1_{secondary\_horizontal\_coma} + M(d1)_{4;15} \times Z1_{secondary\_horizontal\_trefoil} + M(d1)_{4;17} \times Z1_{horizontal\_pentafoil}$$

The extrapolated Zernike coefficient representing the vertical coma value of the extrapolated pupil diameter d2 is based on a weighted vertical coma value relating to the first pupil diameter d1 and, optionally, on a weighted secondary vertical coma value relating to the first pupil diameter d1. In particular, the vertical coma value relating to the first pupil diameter d1 is multiplied with a factor $M_{5;5}$ and, the optional secondary vertical coma value relating to the first pupil diameter d1 is multiplied with a factor $M_{5;14}$. The factor $M_{5;14}$ may increase with increasing pupil diameter d1.

The extrapolated Zernike coefficient representing the vertical coma value of the extrapolated pupil diameter d2 is, optionally, further based on a weighted secondary vertical trefoil value relating to the first pupil diameter d1. In particular, the optional secondary vertical trefoil value relating to the first pupil diameter d1 is multiplied with a factor $M_{5;16}$. The factor $M_{5;16}$ may increase with increasing pupil diameter d1.

The extrapolated Zernike coefficient representing the vertical coma value of the extrapolated pupil diameter d2 is, optionally, further based on a weighted vertical pentafoil value relating to the first pupil diameter d1. In particular, the optional vertical pentafoil value relating to the first pupil diameter d1 is multiplied with a factor $M_{5;18}$. The factor $M_{5;18}$ may increase with increasing pupil diameter d1.

$$Z2_{vertical\_coma} = M(d1)_{5;5} \times Z1_{vertical\_coma} + M(d1)_{5;14} \times Z1_{secondary\_vertical\_coma} + M(d1)_{5;16} \times Z1_{secondary\_vertical\_trefoil} + M(d1)_{5;18} \times Z1_{vertical\_pentafoil}$$

The extrapolated Zernike coefficient representing the horizontal trefoil value of the extrapolated pupil diameter d2 is based on a weighted horizontal trefoil value relating to the first pupil diameter d1 and, optionally, on a weighted secondary horizontal coma value relating to the first pupil diameter d1. In particular, the horizontal trefoil value relating to the first pupil diameter d1 is multiplied with a factor $M_{6;6}$ and, the optional secondary horizontal coma value relating to the first pupil diameter d1 is multiplied with a factor $M_{6;13}$. The factor $M_{6;13}$ may increase with increasing pupil diameter d1.

The extrapolated Zernike coefficient representing the horizontal trefoil value of the extrapolated pupil diameter d2 is, optionally, further based on a weighted secondary horizontal trefoil value relating to the first pupil diameter d1. In particular, the optional secondary horizontal trefoil value relating to the first pupil diameter d1 is multiplied with a factor $M_{6;15}$. The factor $M_{6;15}$ may increase with increasing pupil diameter d1.

The extrapolated Zernike coefficient representing the horizontal trefoil value of the extrapolated pupil diameter d2 is, optionally, further based on a weighted horizontal pentafoil value relating to the first pupil diameter d1. In particular, the optional horizontal pentafoil value relating to the first pupil diameter d1 is multiplied with a factor $M_{6;17}$. The factor $M_{6;17}$ may increase with increasing pupil diameter d1.

$$Z2_{horizontal\_trefoil} = M(d1)_{6;6} \times Z1_{horizontal\_trefoil} + M(d1)_{6;13} \times Z1_{secondary\_horizontal\_coma} + M(d1)_{6;15} \times Z1_{seconday\_horizontal\_trefoil} + M(d1)_{6;17} \times Z1_{horizontal\_pentafoil}$$

The extrapolated Zernike coefficient representing the vertical trefoil value of the extrapolated pupil diameter d2 is based on a weighted vertical trefoil value relating to the first pupil diameter d1 and, optionally, on a weighted secondary vertical coma value relating to the first pupil diameter d1. In particular, the vertical trefoil value relating to the first pupil diameter d1 is multiplied with a factor $M_{7;7}$ and, the optional secondary vertical coma value relating to the first pupil diameter d1 is multiplied with a factor $M_{7;14}$. The factor $M_{7;14}$ may increase with increasing pupil diameter d1.

The extrapolated Zernike coefficient representing the vertical trefoil value of the extrapolated pupil diameter d2 is, optionally, further based on a weighted secondary vertical trefoil value relating to the first pupil diameter d1. In particular, the optional secondary vertical trefoil value relating to the first pupil diameter d1 is multiplied with a factor $M_{7;16}$. The factor $M_{7;16}$ may increase with increasing pupil diameter d1.

The extrapolated Zernike coefficient representing the vertical trefoil value of the extrapolated pupil diameter d2 is, optionally, further based on a weighted vertical pentafoil value relating to the first pupil diameter d1. In particular, the optional the vertical pentafoil value relating to the first pupil diameter d1 is multiplied with a factor $M_{7;18}$. The factor $M_{7;18}$ may increase with increasing pupil diameter d1.

$$Z2_{vertical\_trefoil} = M(d1)_{7;7} \times Z1_{vertical_{trefoil}} + M(d1)_{7;14} \times Z1_{secondary\_vertical\_coma} + M(d1)_{7;16} \times Z1_{secondary\_vertical\_trefoil} + M(d1)_{7;18} \times Z1_{vertical\_pentafoil}$$

Figures 6, 7:
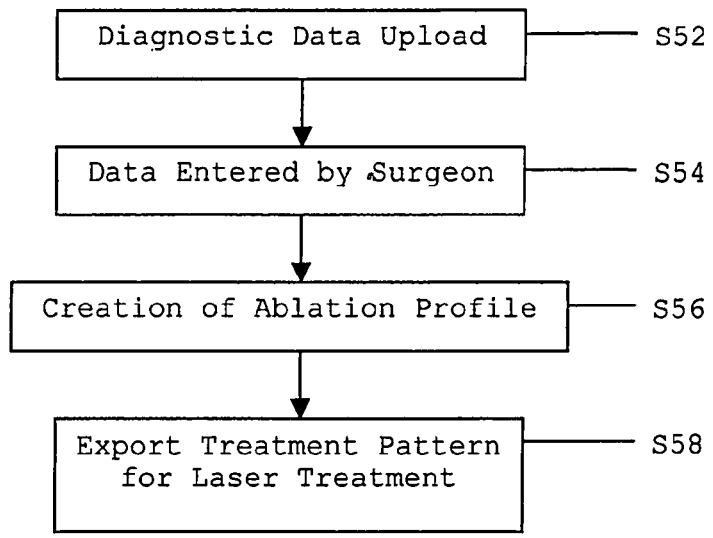
FIG. 6 shows a flow chart relating to the further data processing of diagnostic data according to an embodiment of the invention.
FIG. 7 shows an exemplary static matrix S according to an embodiment of the invention.

FIG. 6 shows a flow chart 600 relating to the further processing of obtained wavefront and topographic data in order to generate a treatment pattern for a vision correction treatment, e.g., a refractive laser treatment.

In step S52, diagnostic data which have been obtained in a preceding step is uploaded. Therefore, the processing of the eye aberration data can be conducted at a different place, e.g., at the laser treatment center or on the surgeon's premises.

In step S54, the surgeon may enter respective data, e.g., he may amend the data to incorporate data based on personal knowledge and experience to adapt the vision correction treatment.

An ablation profile is created in step S56, and a treatment pattern is exported in step S58. The data may be stored for a later vision correction treatment or, alternatively, a treatment may be conducted more immediately.

FIG. 7 shows a static matrix S, 700, and FIG. 8 shows a dynamic matrix D, 800. The dynamic matrix D is multiplied with the pupil diameter d1 to generate the conversion matrix M, as discussed above.

Exemplary conversion matrices M (900, 1000, 1100) are respectively shown in FIGS. 9, 10 and 11. FIG. 9 shows a conversion matrix M (900) for extrapolating wavefront data from 5.0 mm to 5.5 mm. FIG. 10 shows a conversion matrix M (1000) for extrapolating wavefront data from 6.0 mm to 6.6 mm. FIG. 11 shows a conversion matrix M (1100) for extrapolating wavefront data from 7.0 mm to 7.7 mm. The matrices as shown in FIGS. 7 to 11 relate to an extrapolation ratio of 10% and to a myopic wavefront.

With a different extrapolation ratio and/or wavefront, at least one of the static matrix S or the dynamic matrix D comprises different values and/or elements.

The following example is given to show the relation between the values given in the matrix 900 shown in FIG. 9 and the static matrix S (700) shown in FIG. 7 in combination with the dynamic matrix 800 shown in FIG. 8.

Corresponding to FIG. 9 the value $M_{4;4}$ of the conversion matrix M, at least forming a part of the horizontal coma of the extrapolated pupil diameter d2, will be calculated as follows. The respective values of the matrices as shown in FIGS. 7 and 8 will be utilized.

$$M_{4;4}(d1) = S_{4;4} + d1 \times D_{4;4}$$

$$M_{4;4} = 11.127 + d1 \times 0.033$$

The pupil diameter d1 is 5 mm in the example of FIG. 9.

$$M_{4;4} = 1.127 + 5 \times 0.033$$

$$M_{4;4} = 1.292$$

The remaining values for the matrix of FIG. 9 are calculated accordingly. The values, i.e., the conversion matrix M, can be calculated every time or can be generated in advance and stored, e.g., on a readable medium such as a hard-disk or any other appropriate memory.

The matrix according to FIG. 9 corresponds to an extrapolation from a pupil diameter d1=5 mm to a pupil diameter d2=5.5 mm. The values of the matrices as shown in FIG. 10 (d1=6 mm, d2=6.6 mm) and FIG. 11 (d1=7 mm, d2=7.7 mm) are calculated in accordance with the above scheme.

Another example is given relating to an extrapolation from 5 mm to 5.5 mm in accordance with FIG. 9, for calculating the amplitude values of the Zernike polynomials for the extrapolated wavefront aberration data corresponding to the pupil diameter d2.

The horizontal coma (Z310) corresponding to the pupil diameter d2 is calculated as follows:

$$Z2_{310} = M(d1)_{4;4} \times Z1_{310} + M(d1)_{4;13} \times Z1_{510} + M(d1)_{4;15} \times Z1_{530} + M(d1)_{4;7} \times Z1_{550}$$

$$Z_{310}(d2) = 1.292 \times Z310(d1) + 0.648 \times Z510(d1) + (-0.038) \times Z530(d1) + (-0.038) \times Z550(d1)$$

The remaining values of the vector Z2 are calculated accordingly.

While certain embodiments have been chosen to illustrate the invention, it will be understood by those skilled in the art that changes and modifications can be made therein without departing from the scope of the invention as defined in the appended claims.

We claim:

1. A method for vision correction comprising the following steps:
   (a) acquiring wavefront measurements from an eye at a first pupil diameter d1, representing the wavefront measurements by Zernike coefficients, and providing one or more Zernike coefficients relating to the first pupil diameter d1 in a vector Z1;
   (b) multiplying the vector Z1 with a conversion matrix M and outputting the result into a vector Z2 containing extrapolated Zernike coefficients relating to the second pupil diameter d2, wherein the first pupil diameter d1 is incorporated into the conversion matrix M and d2 is greater than d1;
   (c) using the extrapolated Zernike coefficients to determine a vision correction treatment;
   (d) ordering the Zernike coefficients relating to the first pupil diameter d1 into the vector Z1 using a permutation matrix P, prior to the step of multiplying the vector Z1 with the conversion matrix M; and
   (e) applying the treatment to the eye.

2. The method according to claim 1, wherein the conversion matrix M is generated from a static matrix S and a dynamic matrix D, wherein the first pupil diameter d1 is incorporated into the dynamic matrix D.

3. The method according to claim 1, wherein the conversion matrix M is generated by multiplying the pupil diameter d1 with a dynamic matrix D, and adding the multiplication result with a static matrix S.

4. The method according to claim 1, comprising the step of re-ordering the Zernike coefficients relating to the second pupil diameter d2 contained in the vector Z2 using a transposed permutation matrix $P^T$.

5. The method according to claim 1, wherein the Zernike coefficients relating to the first pupil diameter d1 are extrapolated in the range of 1% to 30%.

6. The method according to claim 1, wherein the Zernike coefficients relating to the first pupil diameter d1 are extrapolated in the range of 5% to 20%.

7. The method according to claim 1, wherein the Zernike coefficients relating to the first pupil diameter d1 are extrapolated in the range of 5% to 15%.

8. The method according to claim 1, wherein the Zernike coefficients relating to the first pupil diameter d1 are extrapolated by 10%.

* * * * *